United States Patent
Khen et al.

(10) Patent No.: US 9,392,981 B2
(45) Date of Patent: Jul. 19, 2016

(54) COMPACT GANTRY SYSTEM USING INDEPENDENTLY CONTROLLABLE DETECTORS

(71) Applicant: General Electric Company, Schenectady, NY (US)

(72) Inventors: Roee Khen, Haifa (IL); Jean-Paul Bouhnik, Zichron Yaacov (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/818,473

(22) Filed: Aug. 5, 2015

(65) Prior Publication Data

US 2015/0342543 A1 Dec. 3, 2015

Related U.S. Application Data

(63) Continuation-in-part of application No. 14/612,398, filed on Feb. 3, 2015, which is a continuation of application No. 14/135,751, filed on Dec. 20, 2013, now Pat. No. 9,029,791.

(51) Int. Cl.
| | |
|---|---|
| *G01T 1/10* | (2006.01) |
| *A61B 6/03* | (2006.01) |
| *A61B 6/00* | (2006.01) |
| *G01T 1/161* | (2006.01) |
| *G01T 1/29* | (2006.01) |
| *G06T 11/00* | (2006.01) |

(Continued)

(52) U.S. Cl.
CPC .............. *A61B 6/037* (2013.01); *A61B 6/4258* (2013.01); *A61B 6/4266* (2013.01); *A61B 6/5205* (2013.01); *G01T 1/161* (2013.01); *G01T 1/1648* (2013.01); *G01T 1/2985* (2013.01); *G06T 11/005* (2013.01); *A61B 6/0407* (2013.01); *A61B 6/503* (2013.01); *A61B 6/545* (2013.01); *A61B 6/547* (2013.01)

(58) Field of Classification Search
CPC .............................. G01T 1/161; G01T 1/2985
See application file for complete search history.

(56) References Cited

U.S. PATENT DOCUMENTS

| | | | |
|---|---|---|---|
| 3,774,031 A | 11/1973 | Mallard et al. | |
| 4,204,123 A * | 5/1980 | Stoddart | A61B 6/037 250/363.04 |
| 5,047,641 A | 9/1991 | Besseling et al. | |

(Continued)

FOREIGN PATENT DOCUMENTS

| | | |
|---|---|---|
| EP | 2275989 A1 | 1/2011 |
| WO | 2014165472 A1 | 10/2014 |

OTHER PUBLICATIONS

Non-Final Office Action issued in connection with related U.S. Appl. No. 14/501,337 on May 1, 2015.

(Continued)

*Primary Examiner* — Kiho Kim
(74) *Attorney, Agent, or Firm* — Lucas Divine

(57) ABSTRACT

A gantry system is provided. The gantry system may be used for acquiring image data and reconstructing the image data into output images. Image detectors include a detector arm and detector head. Image detectors are attached to a gantry in a compact configuration such that the image detector head may extend into the bore of a stator. The system can be a Nuclear Medicine (NM) imaging system to acquire Single Photon Emission Computed Tomography (SPECT) image information.

19 Claims, 11 Drawing Sheets

(51) Int. Cl.
*G01T 1/164* (2006.01)
*A61B 6/04* (2006.01)

(56) References Cited

U.S. PATENT DOCUMENTS

| | | | |
|---|---|---|---|
| 5,436,958 A | 7/1995 | Taylor | |
| 5,675,513 A | 10/1997 | Hammer | |
| 5,689,543 A | 11/1997 | Graves et al. | |
| 5,949,842 A | 9/1999 | Schafer et al. | |
| 6,147,353 A * | 11/2000 | Gagnon | G01T 1/166 250/363.04 |
| 6,256,404 B1 | 7/2001 | Gordon et al. | |
| 6,271,524 B1 | 8/2001 | Wainer et al. | |
| 6,279,420 B1 | 8/2001 | Knorowski et al. | |
| 6,636,214 B1 | 10/2003 | Leather et al. | |
| 7,223,240 B2 | 5/2007 | Murashita | |
| 7,280,638 B1 | 10/2007 | Weaver et al. | |
| 7,555,164 B2 | 6/2009 | Lin | |
| 7,755,057 B2 | 7/2010 | Kim | |
| 7,829,856 B2 | 11/2010 | Jansen et al. | |
| 8,194,237 B2 | 6/2012 | Cronin et al. | |
| 8,421,021 B2 | 4/2013 | Sachs et al. | |
| 8,479,213 B2 | 7/2013 | Jones et al. | |
| 8,542,892 B2 | 9/2013 | Kovalski | |
| 8,542,898 B2 | 9/2013 | Bathe et al. | |
| 2004/0262525 A1 * | 12/2004 | Yunker | G01T 1/1648 250/363.08 |
| 2010/0001190 A1 | 1/2010 | Wieczorek et al. | |
| 2014/0343412 A1 | 11/2014 | Wieczorek et al. | |
| 2015/0065873 A1 | 3/2015 | Tsukerman et al. | |

OTHER PUBLICATIONS

Non-Final Office Action issued in connection with related U.S. Appl. No. 14/501,337 on Jun. 11, 2015.
Non-Final Office Action issued in connection with related U.S. Appl. No. 14/327,178 on Sep. 17, 2015.

* cited by examiner

COMPACT GANTRY SYSTEM USING INDEPENDENTLY CONTROLLABLE DETECTORS

PRIORITY AND REFERENCE TO RELATED APPLICATIONS

This application is a continuation-in-part of U.S. patent application Ser. No. 14/612,398, entitled "IMAGING SYSTEM USING INDEPENDENTLY CONTROLLABLE DETECTORS", filed Feb. 3, 2015, which is a continuation of U.S. patent application Ser. No. 14/135,751, entitled "IMAGING SYSTEM USING INDEPENDENTLY CONTROLLABLE DETECTORS", filed Dec. 20, 2013 and patented on May 12, 2015 as U.S. Pat. No. 9,029,791, the disclosures of which is incorporated by reference herein as if set forth in their entirety.

BACKGROUND

The subject matter disclosed herein relates generally to medical imaging systems, and more particularly to Nuclear Medicine (NM) imaging systems which can be Single Photon Emission Computed Tomography (SPECT) imaging systems.

In NM imaging, such as SPECT imaging, radiopharmaceuticals are administered internally to a patient. Detectors (e.g., gamma cameras), typically installed on a gantry, capture the radiation emitted by the radiopharmaceuticals and this information is used to form images. The NM images primarily show physiological function of, for example, the patient or a portion of the patient being imaged.

Conventional SPECT imaging systems include one or two gamma cameras mounted to a single gantry. These gamma cameras do not extend or retract. These gamma cameras do not independently pivot. The gamma cameras are formed from particular materials. In the selection of material, tradeoffs must be made, such as imaging sensitivity, size, cost, etc. Additionally, specific collimation may be provided, which typically limits the application of the scanner to a particular type of scan, such as whole body bone exams, cardiac exams, among other types of scans.

There is a need for gantry systems to be compact to provide a positive patient experience. There is a need for gantry systems to support various imaging configurations to provide flexibility, speed, and cost savings.

BRIEF DESCRIPTION

In accordance with various embodiments, a gantry system is provided that comprises a stator comprising a bore therethrough; a carriage moveably attached to the stator; a plurality of image detectors, each image detector having a detector arm attached to the carriage and a detector head extending from the detector arm in an L-shape configuration; wherein at least one detector head extends into the bore of the stator in the z-direction. The image detectors can be linearly attached to the carriage. The image detectors can be radially attached to the carriage. A plurality of image detectors could be at least ten image detectors. The image detectors can be configured to acquire Single Photon Emission Computed Tomography (SPECT) data or configured to acquire Positron Emission Tomography (PET) data.

The carriage can include a rotor with a rotor bore therethrough, said rotor attached to said stator such that the stator bore and rotor bore create a combined bore; wherein the rotor rotates around the axis of the combined bore; and wherein each detector arm extends into the bore of the rotor but does not extend into the bore of the stator. The carriage can include a rail attached to the stator; wherein the carriage comprises a slider such that the slider is movably attached to the rail. The carriage can include a movement member that is movably attached the stator; and wherein the movement member is straight, and a plurality of the image detectors are perpendicularly attached to the movement member.

Further, at least one detector head can be pivotable with respect to its detector arm. Detector arms can extend and retract. Detector heads can pivot their angle. The system can support a configuration where at least one image detector is extended and activate for the imaging operation; and at least one image detector is retracted and inactive for the imaging operation.

The system can further include a table for positioning a subject of an imaging scan; an image reconstruction device; and wherein the image detectors detect emission data from a subject of an imaging scan who has been placed on the table and the system reconstructs an output image from detected emission data. The system can further include a controller unit to control the movement of the carriage, extension and retraction of an image detector arm, and pivoting of an image detector head; wherein the controller unit may control the carriage, image detector arm, and image detector head based on installation information, an imaging protocol, or user input.

The system can further include an image reconstruction device; an operator console; wherein: an imaging operation is initiated by the operator console; the gantry system performs the imaging operation by receiving emission data from the image detectors and moving at least one of the carriage, a detector arm, or an detector head during the imaging operation to detect emission data at multiple view angles; the gantry system sends the emission data at multiple view angles to the image reconstruction device; and the image reconstruction device reconstructs the emission data into an output image for display on the operator console.

The system can further include a second carriage movably attached to the stator; a second plurality of image detectors attached to said carriage; and wherein the second plurality of image detectors is of a different amount than the initial plurality of image detectors. The system can further include a second carriage movably attached to the stator with a second plurality of image detectors attached thereto; a third carriage movably attached to the stator with a third plurality of image detectors attached thereto; a fourth carriage movably attached to the stator with a fourth plurality of image detectors attached thereto; and wherein each detector head of all image detectors extend into the bore of the stator in the z-direction.

In accordance with various embodiments, an imaging method is provided that includes receiving an imaging operation request; beginning an imaging operation by receiving emission data from a plurality of image detectors at a first imaging position; instructing the movement of a carriage movably attached to a gantry stator, wherein the stator has a bore therethrough, wherein the plurality of image detectors are attached to the carriage such that the image detectors are moved to a second imaging position; and continuing the imaging operation by receiving emission data from the plurality of image detectors at the second imaging position. Further, each image detector has a detector arm attached to the carriage and a detector head extending from the detector arm in an L-shape configuration; wherein at least one detector head extends into the bore of the stator in the z-direction. Further, the carriage may comprise a rotor, a slider, or movement member.

DETAILED DESCRIPTION

Figure 1:
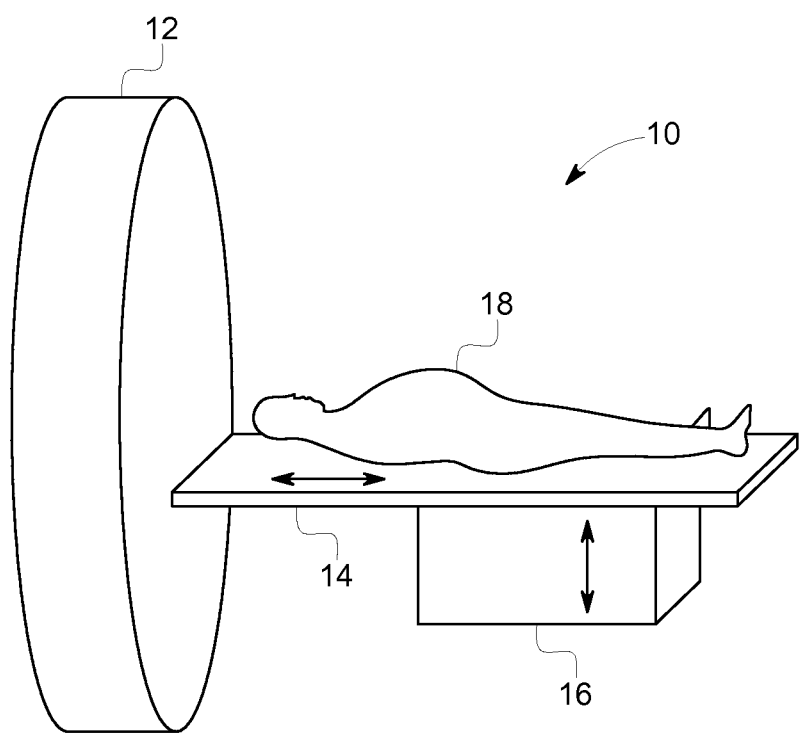
FIG. 1 is a perspective view of an imaging system, in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a medical imaging system, and in particular, a Nuclear Medicine (NM) imaging system having a gantry with a plurality of different types of imaging detectors mounted thereto. For example, in various embodiments of an NM imaging system, a Single Photon Emission Computed Tomography (SPECT) imaging scanner is provided that includes a plurality of detectors with a combination of different types of detectors that acquire SPECT image information. The various embodiments may include detectors formed from different materials, having different configurations or arrangements, having different collimation, etc. The system may be configured to perform single isotope or multi-isotope imaging.

It should be noted that although the various embodiments are described in connection with a particular NM imaging system, such as a SPECT detector system, the various embodiments may be implemented in connection with other imaging systems, such as a Positron Emission Tomography (PET) imaging system. Additionally, the imaging system may be used to image different objects, including objects other than people.

FIG. 1 is a perspective view of an imaging system, in accordance with an embodiment. An imaging system 10 may be provided as illustrated in FIG. 1. A subject 18 can be a human patient in an embodiment. It should be noted that subject 18 does not have to be human. It can be another living creature or inanimate object in various embodiments. Subject 18 can be placed on a table 14, also called pallet, that can move a subject horizontally for locating the subject in the most advantageous imaging position. This horizontal movement in FIG. 1 is the z-direction. Bed mechanism 16 can raise and lower the table 14 vertically for locating the subject in the most advantageous imaging position. This vertical movement in FIG. 1 is the x-direction. A gantry 12 is shown as circular in one embodiment. Gantry 12 includes a bore for insertion of subject 18. In other embodiments gantry 12 may be of any shape such as square, oval, "C" shape, or hexagonal.

Figure 2:
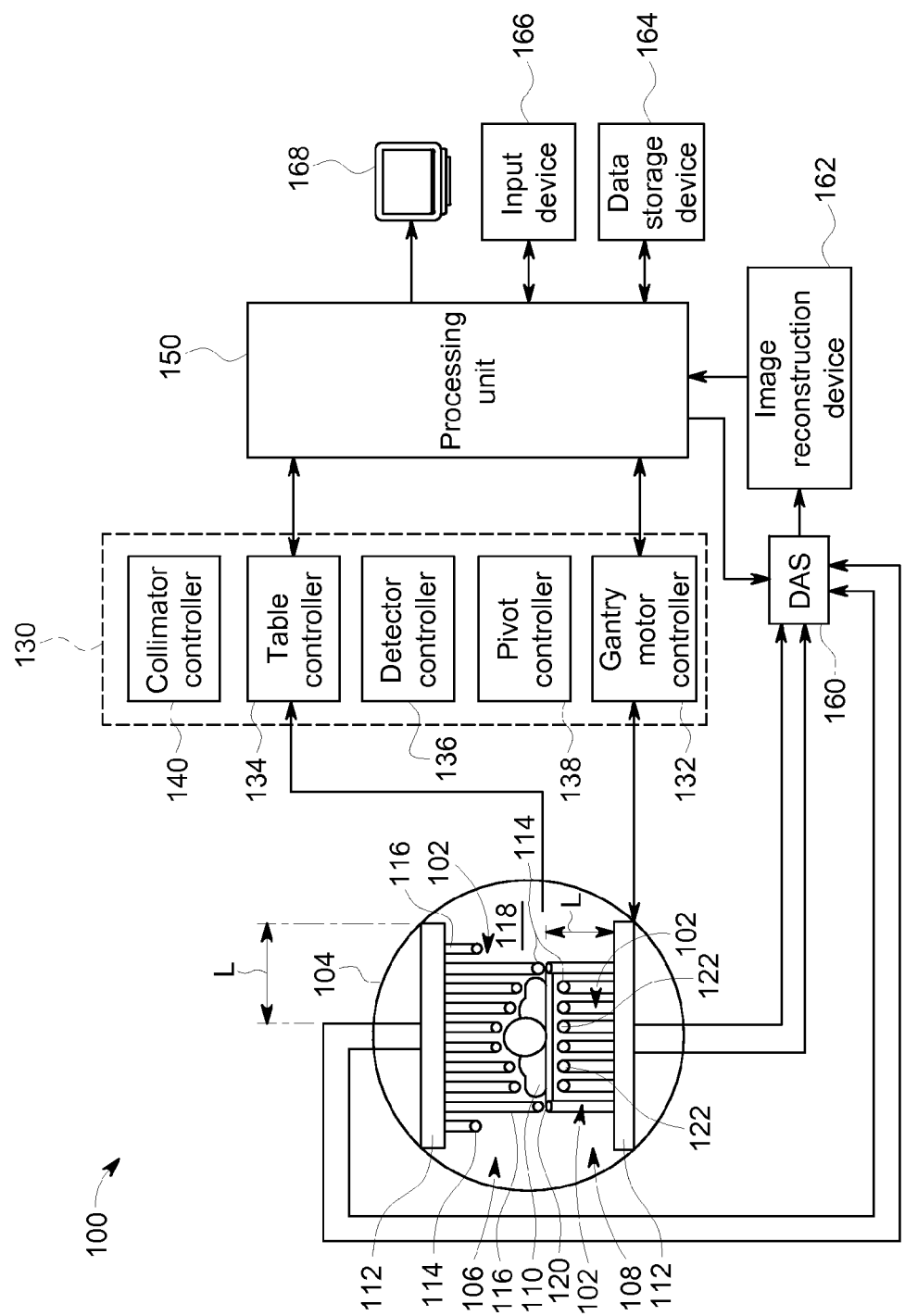
FIG. 2 is a schematic block diagram of an imaging system, in accordance with an embodiment.

FIG. 2 is a schematic block diagram of an imaging system, in accordance with an embodiment. Imaging system 100 has a plurality of image detectors mounted on a gantry. In particular, a plurality of image detectors 102 are mounted to a gantry 104. Various configurations of this attachment will be discussed throughout. In the illustrated embodiment, the imaging detectors 102 are configured as two separate detector arrays 106 and 108 coupled to the gantry 104 above and below a subject 110 (e.g., a patient). The detector arrays 106 and 108 may be coupled directly to the gantry 104, or may be coupled via support members 112 to the gantry 104 to allow movement of the entire arrays 106 and/or 108 relative to the gantry 104 (e.g., translating movement in the left or right direction). Support members 112 may be attached to the gantry 104 through at least one movable support arm or other means. Additionally, each of the image detectors 102 includes a detector head 114 mounted to a movable detector carrier 116 (e.g., a support arm or actuator that may be driven by a motor to cause movement thereof) that extends from the gantry 104. In some embodiments, detector carriers 116 allow movement of the detector heads 114 towards and away from the subject 110, such as linearly, radially, and/or in parallel to each other. Thus, in the illustrated embodiment the detector arrays 106 and 108 are mounted in parallel above and below the subject 110 and allow linear movement of detector heads 114 in a single direction (indicated by the arrow L), illustrated as perpendicular to the support member 112 (that are coupled generally horizontally on the gantry 104). However, other configurations and orientations are possible as described herein.

Each of the image detectors 102 in various embodiments are smaller than a conventional whole body or general purpose imaging detector. A conventional image detector may be large enough to image most or all of a width of a patient's body at one time and may have a diameter of approximately 40 cm. In contrast, each of the imaging detectors 102 may include one or more detector heads 114 coupled to a respective detector carrier 116 may be formed of Cadmium Zinc Telluride (CZT) tiles or modules. For example, each of the detector heads 114 may be 8×8 cm in size and be composed of a plurality of CZT pixelated modules (not shown). For example, each module may be 4×4 cm in size and have 16×16=256 pixels. In some embodiments, each detector head 114 includes a plurality of modules, such as an array of 1×7 modules. However, different configurations and array sizes are contemplated including, for example, detector heads 114 having multiple rows of modules.

It should be understood that the image detectors 102 may be different sizes and/or shapes with respect to each other, such as square, rectangular, circular or other shape. An actual field of view (FOV) of each of the image detectors 102 may be directly proportional to the size and shape of the respective image detector.

Gantry 104 may be formed with a bore 118 (e.g., opening or aperture) therethrough as illustrated. A patient table 120 is configured with a support mechanism to support and carry subject 110 in one or more of a plurality of viewing positions within the bore 118 and relative to the image detectors 102. Alternatively, gantry 104 may comprise a plurality of gantry segments (not shown), each of which may independently move a support member 112 or one or more of the image detectors 102.

Gantry 104 may also be configured in other shapes, such as a "C", "H" and "L", for example, and may be rotatable about subject 110. For example, gantry 104 may be formed as a closed ring or circle, or as an open arc or arch which allows subject 110 to be easily accessed while imaging and facilitates loading and unloading of the subject 110, as well as reducing claustrophobia in some subjects.

Additional image detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110) image data specific for a larger FOV may be acquired more quickly.

Each detector head 114 has a radiation detection face, which is directed towards subject 110 or a region of interest within the subject. The radiation detection faces are each covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimator. In some embodiments, at least two types of collimators are used. Optionally, multi-bore collimators may be constructed to be registered with pixels of the detector heads 114, which in one embodiment are CZT detectors. However, other materials may be used. Registered collimation may increase spatial resolution by forcing photons going through one bore to be collected primarily by one pixel. Additionally, registered collimation may increase sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 130 may control the movement and positioning of the patient table 120, image detectors 102, detector heads 114, gantry 104, support members 112, and/or the collimators 122. Controller unit 130 may have a gantry motor controller 132, table controller 134, detector controller 136, pivot controller 138, and collimator controller 140. The controllers 130, 132, 134, 136, 138, 140 may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, gantry controller 132 may cause image detectors 102 and/or support members 112 to rotate about subject 110.

Table controller 134 may move patient table 120 to position the subject 110 relative to image detectors 102. Patient table 120 may be moved in up-down directions, in-out directions, and right-left directions, for example. The detector controller 136 may control movement of each of image detectors 102 to move closer to and farther from a surface of subject 110, such as by controlling translating movement of the detector carriers 116 linearly towards or away from the subject 110 (e.g., sliding or telescoping movement). Optionally, detector controller 136 may control movement of the detector carriers 116 to allow coordinated move of the detector array 106 or 108. For example, the detector controller 136 may control lateral movement of the detector carriers 116 illustrated by the L arrow. In some embodiments, proximity sensors may be used to guide the controllers to bring the detectors 102 in proximity to (e.g., within close range, such as 1-5 cm) from subject 110 without colliding with or contacting subject 110. Alternatively or additionally, the shape of subject 110 (e.g., patient shape) may be known from imaging the subject 110 with another modality such as CT or 3D optical imaging and the information regarding the shape of the subject 110 used to position the detectors 102. Optionally, in some embodiments, at least some of the detectors 102 include a Pressure Sensing Device (PSD) capable of detecting physical contact of a sensor with the subject 110 or other solid objects and prevent or halt motion of at least one of the detectors 102, patient table 120, or gantry 104 that may, for example, cause harm to subject 110.

The pivot controller 138 may control pivoting movement of the detector heads 114 at ends of the detector carriers 116 and/or pivoting movement of detector carrier 116. For example, one or more of detector heads 114 or detector carriers 116 may be rotated about at least one axis to view the subject 110 from a plurality of angular orientations. The collimator controller 140 may adjust a position of an adjustable collimator, such as a collimator with adjustable strips (or vanes) or adjustable pinhole(s).

Motion of one or more imaging detectors 102 may be in directions other than strictly axially or radially, and optionally, motions in several motion directions may be used. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of subject 110 or a portion of subject 110, the image detectors 102, gantry 104, patient table 120 and/or collimators 122 may be adjusted as discussed in more detail herein, such as to first or initial imaging positions, as well as subsequent imaging positions. The image detectors 102 may each be positioned to image a portion of subject 110. Alternatively, one or more image detectors 102 may not be used to acquire data, such as the imaging detectors 102 at ends of the detector arrays 106 and 108, which may be in a retracted position away from subject 110. Positioning may be accomplished manually by the operator and/or automatically, which may include using other images acquired before the current acquisition, such as by another imaging modality such as CT, MRI, X-Ray, PET or ultrasound. Additionally, detector heads 114 may be configured to acquire non-NM data, such as x-ray CT data.

After image detectors 102, gantry 104, patient table 120, and/or collimators 122 are positioned, one or more images are acquired by one or more of the imaging detectors 102 being used. The image data acquired by each imaging detector 102 may be combined and reconstructed into a composite image, which may comprise two-dimensional (2D) images, a three-dimensional (3D) volume or a 3D volume over time (4D).

In one embodiment, the image detectors 102, gantry 104, patient table 120, and/or collimators 122 remain stationary after being initially positioned. In another embodiment, an effective field of view for one or more of the imaging detectors may be increased by movement such as pivoting one or more of the imaging detectors 102, rotating one or more of the detector arrays 106 and/or 108 with respect to the gantry, adjusting one or more of the collimators 122, or moving the patient table 120.

In various embodiments, a data acquisition system (DAS) 160 receives electrical signal data produced by image detectors 102 and converts this data into digital signals for subsequent processing. An image reconstruction device 162 and a data storage device 164 may be provided in addition to processing unit 150. It should be noted that one or more functions related to one or more of data acquisition, motion control, data processing and image reconstruction may be accomplished through hardware, software and/or by shared processing resources, which may be located within or near the imaging system 100, or may be located remotely. Additionally, a user input device 166 may be provided to receive user inputs (e.g., control commands), as well as a display 168 for displaying images. User input device 166 and display 168 may be combined in an operator console. Other outputs may be in the system, such a printer, a computer network, or television.

An embodiment includes two detector arrays 106 and 108 (in opposed parallel alignment) that allow movement of a plurality of detector heads 114. In this embodiment, the two detector arrays 106 and 108 are top and bottom detector arrays, respectively, wherein the subject 110 is positioned there between on the patient table 120 with the detector array 106 above the subject 110 and the detector array 108 below the subject 110. As can be seen, the detector heads 114 of the detector arrays 106 or 108 are generally supported along a plane of the support member 112 and moveable relative thereto. For example, the support members 112 may be generally planar with each of the detector heads 114 moveable with respect to the support member 112 such that the detector heads 114 move along parallel axes relative to the plane of the support member 112 (e.g., perpendicular to the plane of the support member 112 while maintaining a parallel relationship). In some embodiments, the support members 112 of the detector arrays 106 and 108 are also arranged in an H-type configuration or parallel to each other. In one embodiment, the lower support member 112 is coupled to the patient bed 120 (or other bed support) such that lower support member 112 moves up and down with the patient bed 120. Alternatively, in some embodiments, the lower support member 112 is configured to move in unison with the up/down bed motion (e.g., moved simultaneously or concurrently with the patient bed 120), but may not be coupled to the patient bed 120.

In this embodiment, each of the detector heads 114 of the detector array 106 is individually and independently controllable to translate the detector heads 114 upwards and downwards with respect to the subject 110. For example, one or more of the detector heads 114 in the detector array 106 is operable to translate down until the detector head 114 is proximate or adjacent the subject's body, while not contacting or colliding with the subject 110. The distance of the detector heads 114 from the subject 110 may be controlled using one or more proximity sensors as known in the art. Thus, as shown, a plurality of the detector heads 114 of the detector array 106 are moved towards and positioned proximate or adjacent subject 110 (wherein some of the detector heads 114 are positioned at different distances from the support member 112 than other detector heads 114).

It should be noted that optionally the support member 112 may be moved to facilitate positioning of the detector heads 114. For example, depending on the size of subject 110 and the maximum length of detector carriers 116, support member 112 of detector array 106 may likewise move towards or away from subject 110, such that all of the detector heads 114 are moved together to a position closer or farther from the subject 110 (e.g., coarse movement) with the individual detector heads 114 thereafter moved to position each in proximity or adjacent to subject 110 (e.g., fine tuning movement). The support members 112 also may provide other optional movement, such as later movement as illustrated by the L arrows. For example, depending on the size or shape of the subject 110 and the positioning of the patient table 120, support member 112 may initially translate to align detector array 106 in a direction parallel to the coronal plane of subject 1q0.

The positioning of the plurality of detector heads 114, in particular each of the individual detector heads 114 in the detector array 106 and/or 108 may be provided at the same time (e.g., concurrently or simultaneously) or at different times (e.g., sequentially).

In operation, once positioned, one or more of the detector heads 114 of the detector array 106 may rotate, for example, along the examination axis and/or transverse (e.g., perpendicular) to the examination axis to view the subject 110 from a plurality of different orientations. The movement of the detector heads 114 may be, for example, stepwise or continuous through a range of motion. The detector heads 114 of the detector array 108 likewise may rotate. The detector heads 114 of the detector arrays 106 and 108 may rotate at the same time (e.g., concurrently or simultaneously) or may rotate at different times (e.g., sequentially). The imaging by each of the image detectors 102 may be performed simultaneously, concurrently, or sequentially.

Figure 3:
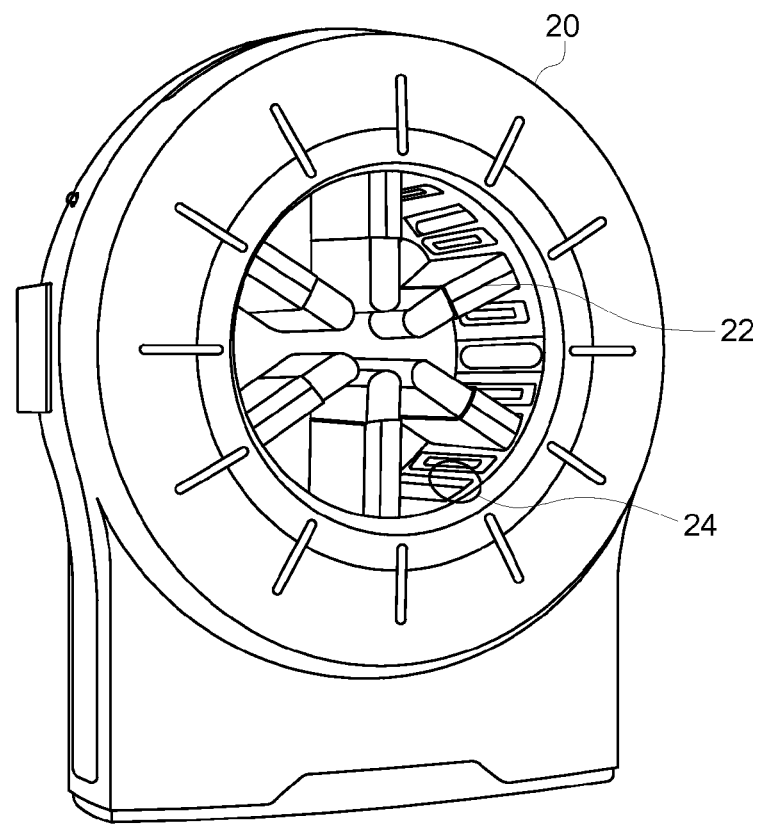
FIG. 3 is a perspective view of a gantry design with detectors placed in a radial configuration, in accordance with an embodiment.

FIG. 3 is a perspective view of a gantry design with detectors placed in a radial configuration, in accordance with an embodiment. FIG. 3 shows a gantry 20 that can support twelve image detectors 22. The gantry 20 can contain the features of the FIG. 2 system in one embodiment. Image detectors 22 can extend and retract, with further reference to FIG. 4. Image detectors 22 can rotate around the center of the bore on a rotor, with further reference to FIG. 8.

Only six image detectors 22 have been installed in gantry 20. This could be for lower cost of the system, easier maintenance, or other reasons, for example. Thus, the system of FIG. 3 is a partially populated imaging system. It is partially populated because the installation information for the system indicates that the system can support twelve image detectors 22, but only six image detectors 22 are installed. The locations where a detector column can be installed or attached can be called receiver locations 24 in some embodiments. The image detectors 22 in FIG. 3 are shown in a radially extended position.

Installation information can be dynamically updated by processing unit 150 based on information from installation verification elements in receiver locations 24, and stored in data storage device 164 in one embodiment. Installation verification elements can be any sort of switch, button, sensor, or other device that detects the presence of hardware installed or not installed in the system. Installation verification elements of receiver locations 24 are one way that the system can detect and update installation information. Installation information in one embodiment relates to the image detector 22 being physically attached to gantry 20. Further, installation information in another embodiment detects both physical attachment plus a fully functioning arm. In this embodiment, if any of the radial motion motor 48, sweep motor 52, and/or detector elements 54 are inoperable, even though the image detector 22 is attached to the gantry 20, the installation information could indicate the detector column as uninstalled and/or inoperable. Installation information can also indicate the population of specific detector elements 54, as further discussed below. Installation information is also called configuration information in some embodiments. This is because installation information gives information related to the current hardware configuration in the imaging system, and can be dynamically updated. Thus, installation information, sometimes called configuration information, is not just the initial setup information of the system when delivered to a customer, but is information dynamically updated based on many hardware factors throughout the lifetime of the system.

Figure 4:
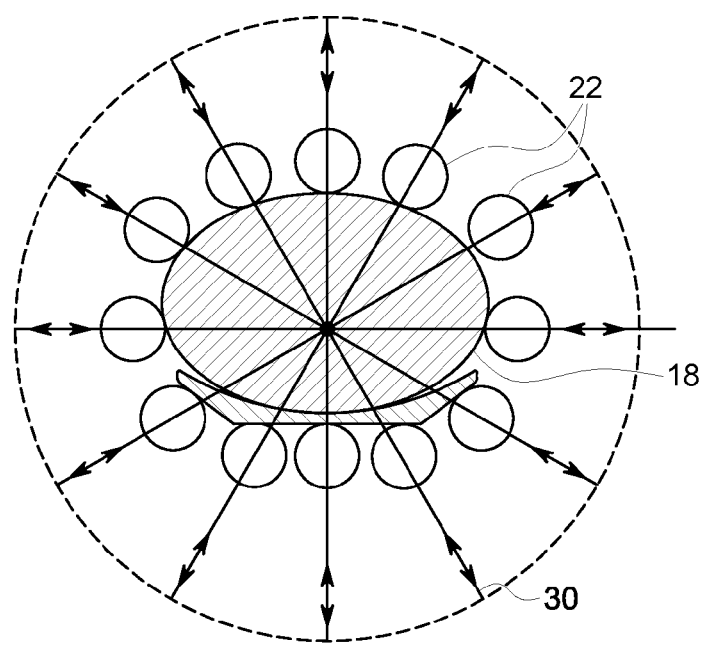
FIG. 4 is a diagram of detectors controlled to move at different points of their radial axis to best scan the specific shape of a subject, in accordance with an embodiment.

FIG. 4 is a diagram of detectors controlled to move at different points of their radial axis to best scan the specific shape of a subject, in accordance with an embodiment. FIG. 4 shows a radial construction of an imaging system where twelve image detectors 22 are placed at a consistent angle, thirty degrees in this example, from each other along the inside of a gantry bore. Thus, the image detectors 22 are uniformly distributed in this example. Each image detector 22 is movable along a radial axis. This allows the image detectors 22 to be closer or further from a subject 18 for imaging. The circles in the figure depict the location of the detector head 50 of image detector 22. The image detectors are shown along the dotted line as their outer limit position in this view of one embodiment. The dual head radial arrows depict the in-out direction of motion of the image detectors 22.

Figure 5:
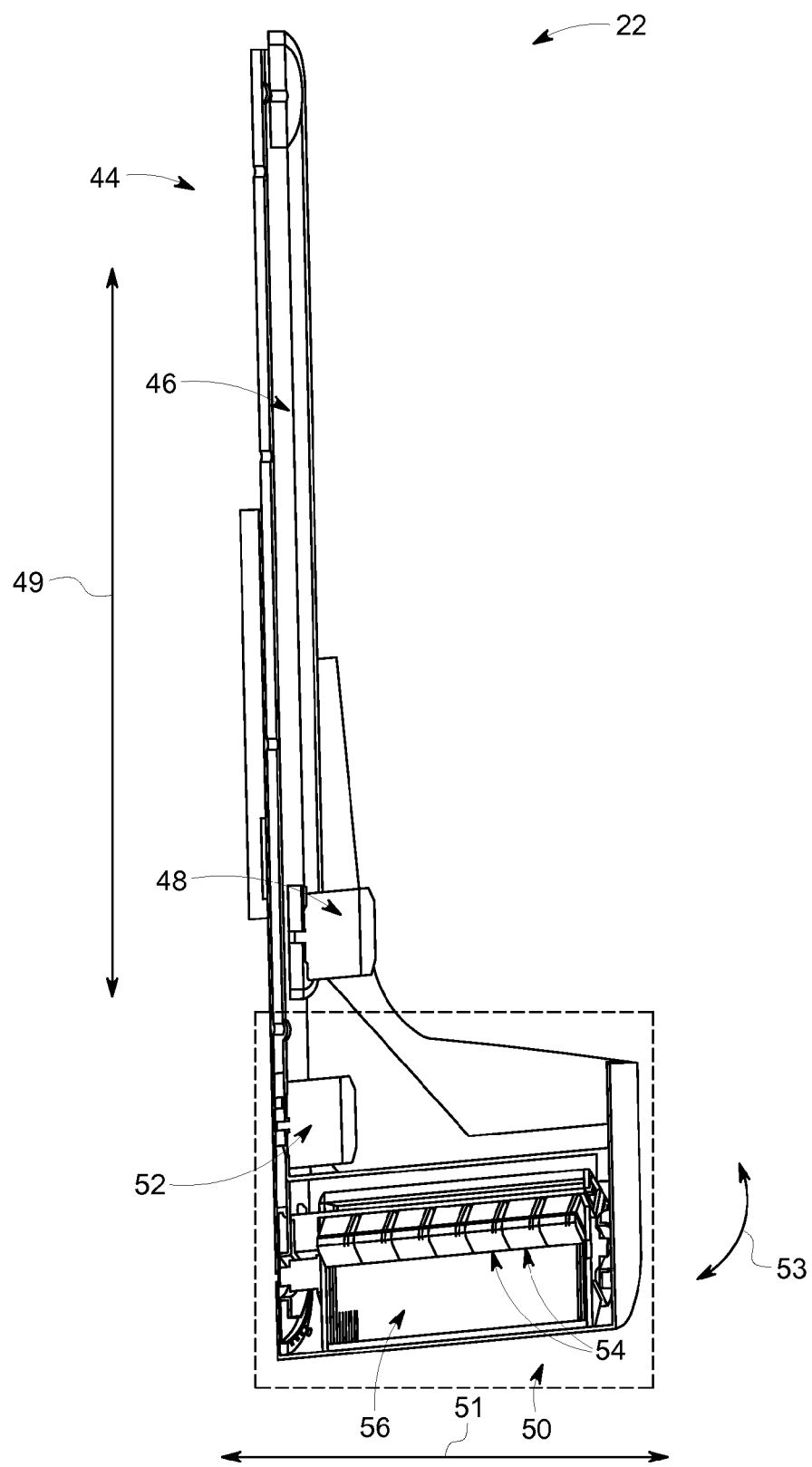
FIG. 5 is a diagram of an imaging detector, in accordance with an embodiment.

FIG. 5 is a diagram of an imaging detector, in accordance with an embodiment. Column arm 44 attaches to a gantry and provides support for and includes a radial motion rail 46, radial motion motor 48, and detector head 50. The radial motion motor 48 controls the movement of the detector head 50 by extending or retracting the detector head 50 along the radial motion rail 46. This provides customizability and flexibility to the imaging system. The detector column can include telescopic covers that allow it to extend and contract as it moves radially in and out along direction 49.

Detector head 50 extends outwards from detector arm 44 along direction 51, forming an "L" configuration according to an embodiment. Detector head 50 includes a sweep motor 52, detector elements 54, and collimator 56. Detector elements 54 can be CZT modules or other detector element modules discussed throughout for detecting imaging data. Sweep motor 52 controls the rotation angle of the detector head 50 in relation to the arm 44. The sweep pivoting axis 53 shows the rotation angle axis of the detector head 50. The detector controller 30 can provide instruction and control to either or both of the radial motion motor 48 and sweep motor 52. Thus, each image detector 22 is independently controllable in the radial location as well as the angle of tilt of detector head 50. The radial motion motor 48 and sweep motor 52 can be two separate motors as shown in the embodiment of FIG. 5. Alternatively, the functionality of the two motors may be provided by one motor.

Figure 6:
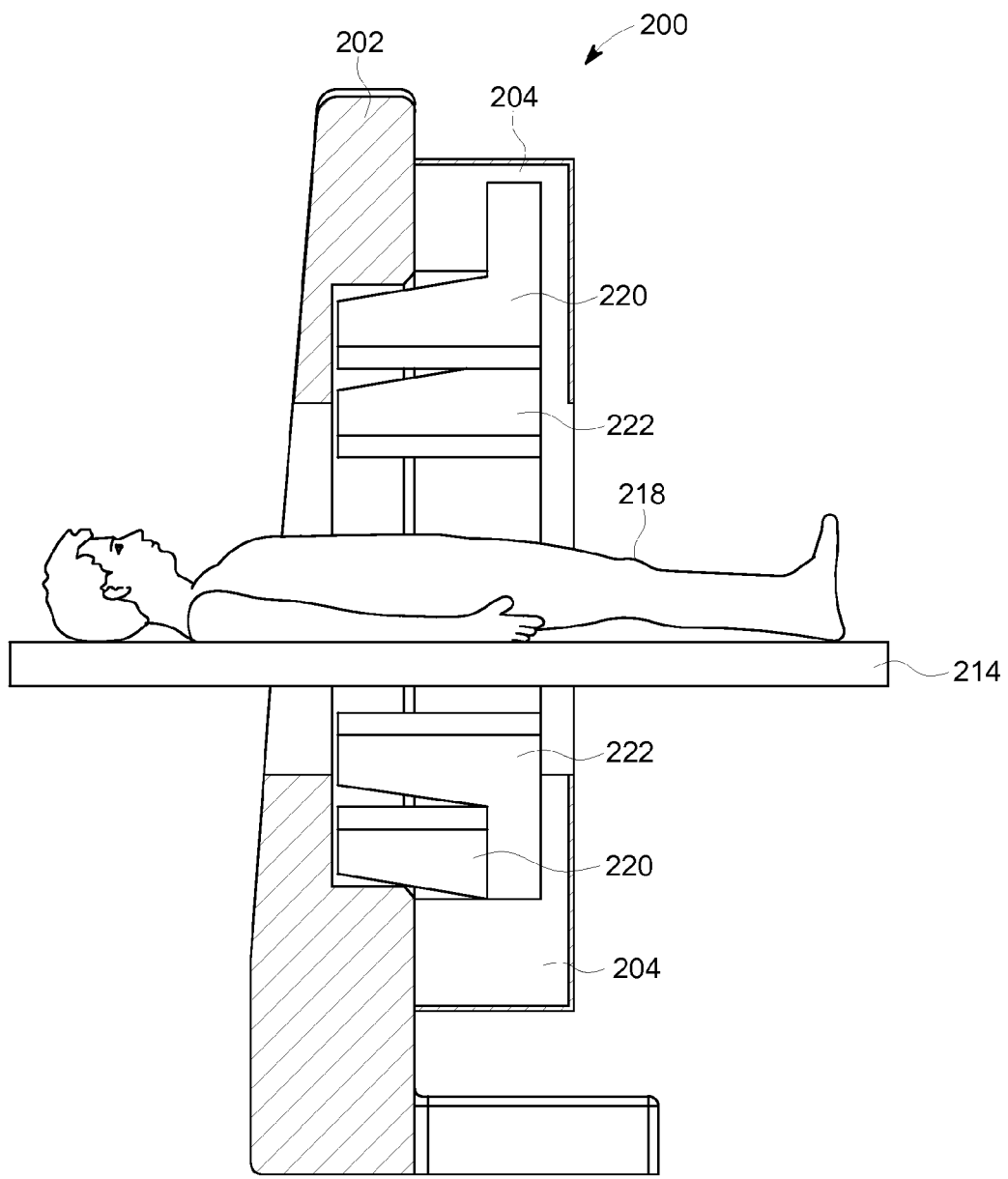
FIG. 6 is a side view of a compact gantry system, in accordance with an embodiment.

FIG. 6 is a side view of a compact gantry system, in accordance with an embodiment. The gantry system 200 includes a stator 202. Carriage 204 is attached to stator 202 so as to provide movement to the image detectors with respect to stator 202. This may be done in various ways as shown throughout in various embodiments. In an embodiment, carriage 204 may be a rotor attached to stator 202 so as to rotate around a center axis of the bore. This can be done through a main bearing and slip ring, or other means.

Retracted image detectors 220 and extended image detectors 222 are attached to carriage 204. Patient 218 is shown positioned on table 214 inside the gantry bore. Retracted image detectors 220 are retracted further from patient 218 and may be chosen to not be used in a current imaging operation. Extended image detectors 222 are extended closer to patient 218 and will likely be used in a current imaging operation.

Retracted image detectors 220 and extended image detectors 222 are shown in an "L" configuration as discussed above with respect to FIG. 5. The extended lower portion of the "L" extends into the bore of stator 202 along the z-direction. Because the image detectors extend into the stator 202 bore instead of outward away from the stator as may be implemented in other systems, the system can be more compact, helping patients, hospitals, and other users of the imaging system. Patients are assisted by not having as deep of a bore, providing better patient visibility and comfort. Hospitals and other medical centers can fit such a compact gantry system into smaller spaces than other systems.

Figure 7:
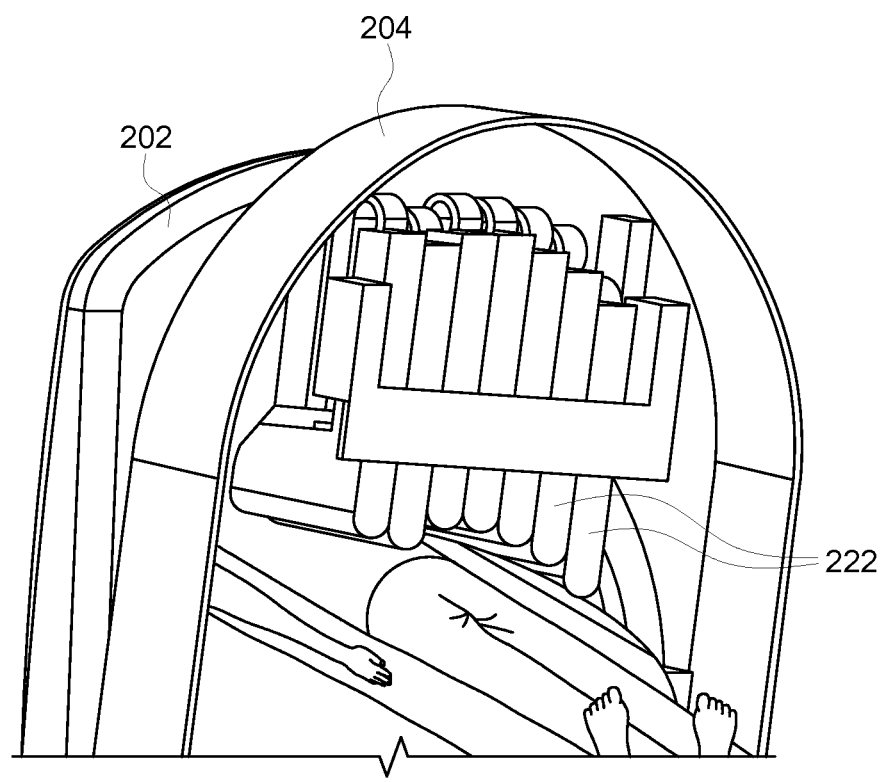
FIG. 7 is a perspective view of a compact gantry system with linear detector alignment, in accordance with an embodiment.

FIG. 7 is a perspective view of a compact gantry system with linear detector alignment, in accordance with an embodiment. Stator 202 is shown. In an embodiment where the system is a multi-modality system, stator 202 may include a CT, MR, or other imaging system within. Carriage 204 is shown as a rotor that includes a linear configuration of image detectors. Image detectors are shown in parallel to each other. In this embodiment, image detectors are shown as extended image detectors 222. During an image scan, the rotor will rotate the extended image detectors 222 around a subject, with the extended image detectors retracting and extending during rotation so as to be close to the imaging subject for improved image output. FIG. 7 only shows a partial view of the gantry system, as additional detectors may be installed in carriage 204 around the circumference of carriage 204.

Figure 8:
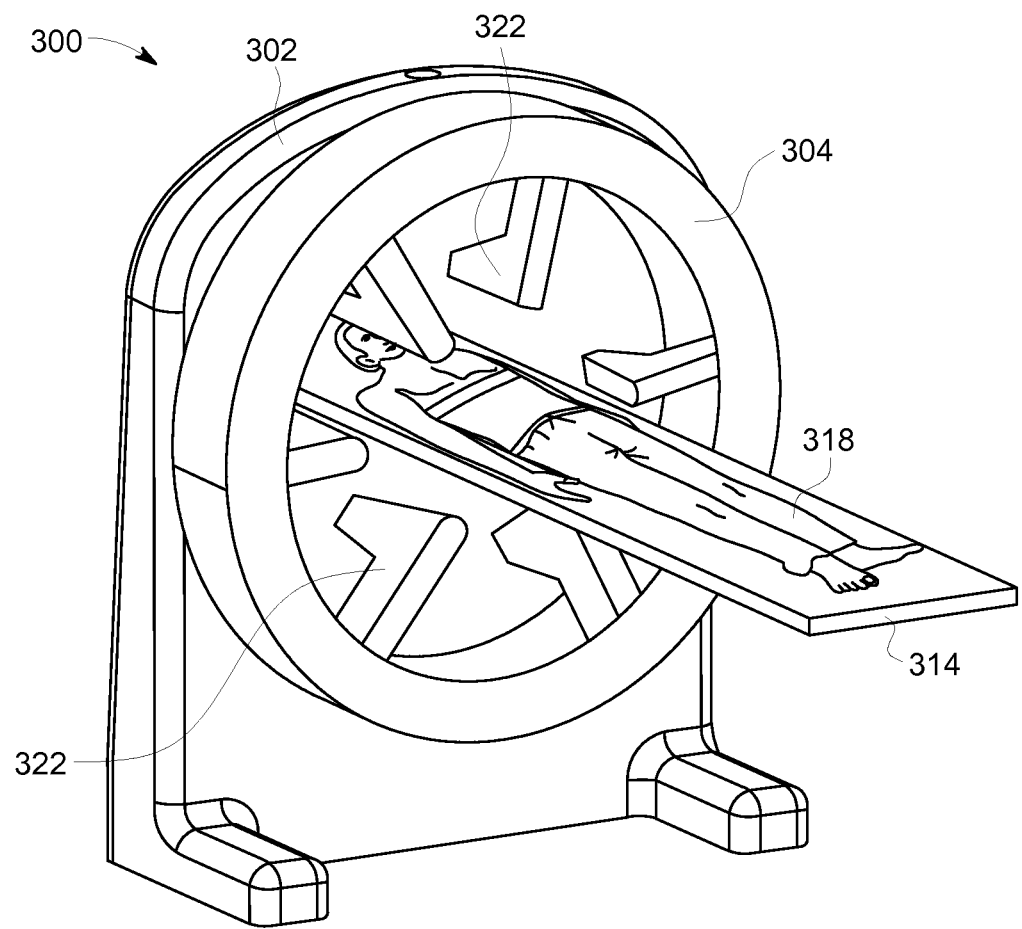
FIG. 8 is a perspective view of a compact gantry system with radial detector alignment, in accordance with an embodiment.

FIG. 8 is a perspective view of a compact gantry system with radial detector alignment, in accordance with an embodiment. Gantry system 300 includes stator 302, rotor 304, image detectors 322, table 314, and subject 318. Image detectors 322 are attached to rotor 304 which rotates image detectors 322 around the center of the combined bore. The combined bore includes the stator bore and the rotor bore.

Image detectors 322 may operate in telescopic radial motion. Image detectors 322 are shown in a compact gantry configuration in that the detector head extends into the bore of the stator.

Only six image detectors are extended in FIG. 8. This could be because the system is only partially populated, as in the embodiment of FIG. 3. As an alternative, as in the embodiment of FIG. 9, the system only has extended the six image detectors shown and kept remaining image detectors retracted and hidden by the rotor cover. For some imaging scans, such as a brain scan, image detectors 322 can extend very close to the subject. In order to prevent detector collision and prevent unneeded usage and wear on image detector hardware, the system may only need to extend a partial amount of the image detectors to perform the scan.

Figure 9:
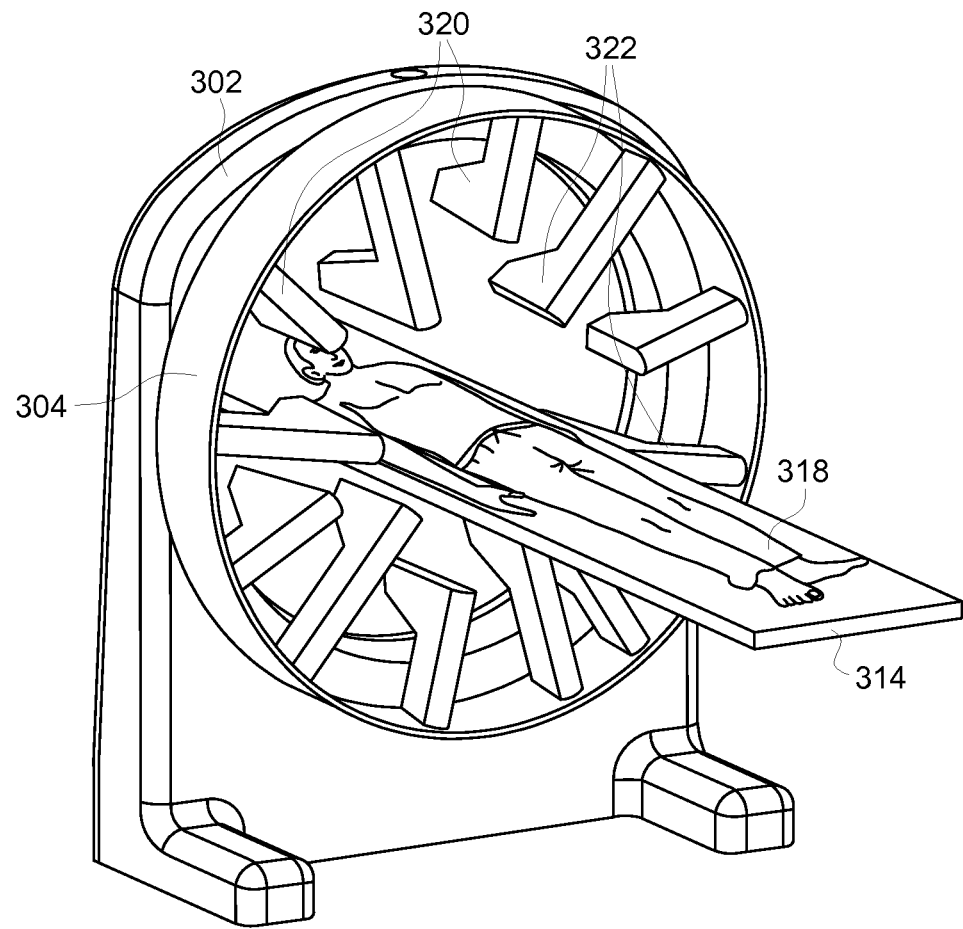
FIG. 9 is a detailed view of a compact gantry system with radial detector alignment, in accordance with an embodiment.

FIG. 9 is a detailed view of a compact gantry system with radial detector alignment, in accordance with an embodiment. FIG. 9 shows the system without rotor cover for ease of explanation. FIG. 9 includes extended image detectors 322 and retracted image detectors 320. The system may extend and retract image detectors before, during, and after an imaging scan. Both extended image detectors 322 and retracted image detectors 320 are in substantially "L" shape configurations with their detector heads extending into the bore of stator 302.

Figure 10:
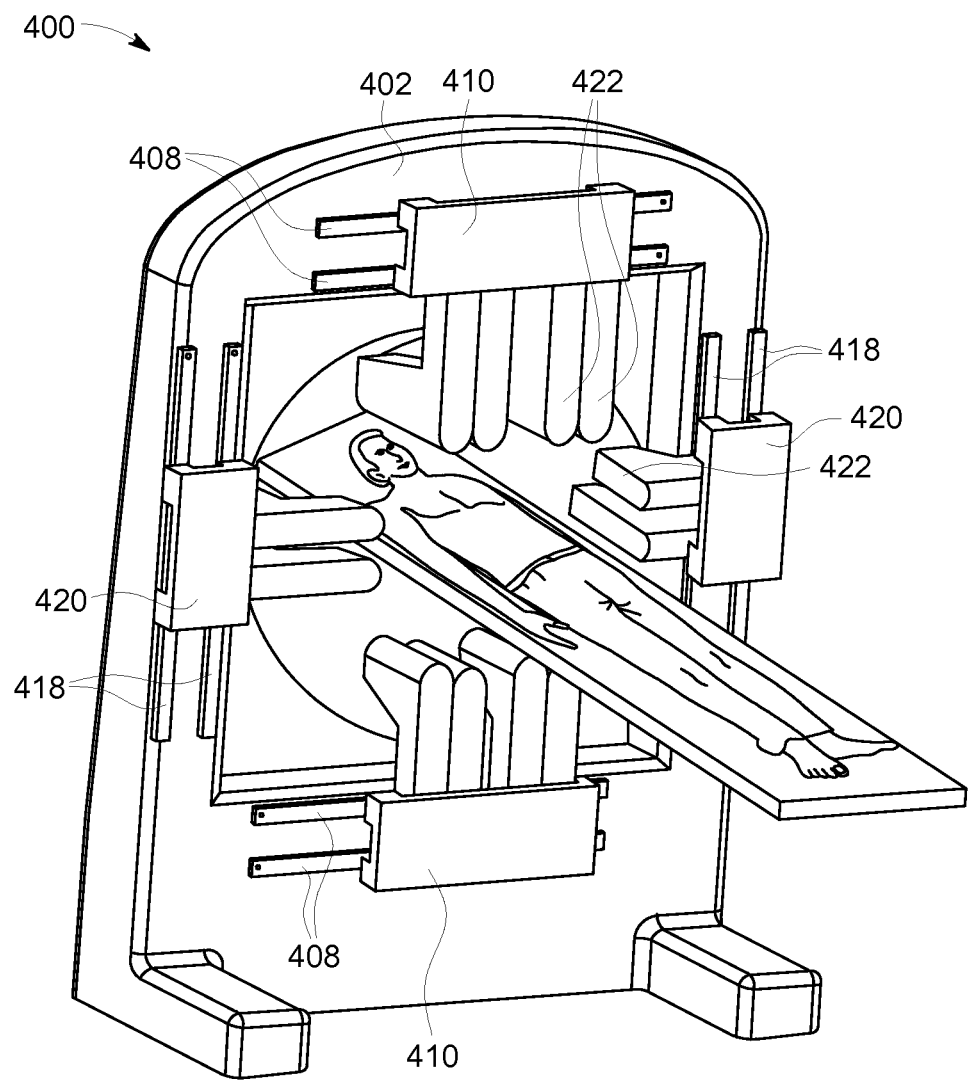
FIG. 10 is a perspective view of a gantry system with linear rails supporting linear detectors, in accordance with an embodiment.

FIG. 10 is a perspective view of a gantry system with linear rails supporting linear detectors, in accordance with an embodiment. Gantry system 400 includes stator 402. Horizontal rails 408 and vertical rails 418 are attached to stator 402. Rails may be singular, dual as shown in FIG. 10, or include three or more. Horizontal sliders 410 are movably attached to horizontal rails 408. Vertical sliders 420 are movably attached to vertical rails 418. Each slider may move independently from other sliders. Horizontal sliders 410 and vertical sliders 420 move along the rails to position the sliders, and attached image detectors 422, at various positions along the gantry system. Sliders may be powered by motors or other mechanical driving means. A slider may be referred to as a movement member.

Image detectors 422 are attached to both vertical sliders 420 and horizontal sliders 410. Image detectors 422 may extend in a perpendicular fashion from their respective sliders as is shown in FIG. 10, or may be attached at various angles thereto. Image detectors 422 thus may extend out from their respective slider and retract towards their respective slider.

The gantry system may move the image detectors before, during, and after an imaging operation. Individual image detectors may be adjusted to scan very specific regions of interest of a subject. If certain image detectors have different characteristics than others (due to image detection materials, wider range of detector head pivot, multi-rows of detector elements, or additional detector characteristics), they may be positioned differently. The system can detect such characteristics as installation information and can use the installation information to make decisions as to how to position certain image detectors for particular imaging operations on particular subjects.

As an example, if the patient of FIG. 10 has an imaging operation related to a right shoulder as the ROI, the system can tailor the image detector positions to best support such a situation. Horizontal sliders 410 can both slide towards the left to position their respective image detectors 422 closer to the ROI. Left vertical slider 420 may extend out both image detectors 422 towards the shoulder. Right vertical slider 420 may keep both image detectors 422 retracted and unused during the imaging scan, as they may be too far from the ROI. This may save electrical costs and prevent unneeded wear on them mechanical parts of unused image detectors. Similarly, the horizontal sliders 410 may only extend out two of their four image detectors if the ROI did not need more coverage than that. After an extension of the image detectors, the detector heads may sweep, or pivot, during the imaging scan to get increased field of view and image data for image reconstruction.

As can be seen from FIG. 10, the gantry system is customizable in an embodiment. Horizontal sliders 410 are shown as carrying four image detectors 422, and vertical sliders 420 are shown as carrying two image detectors 422. The system can support various sizes of sliders that can support a variety of numbers of image detectors. Thus, a hospital site can purchase a lower priced system with less image detectors, for example, and then upgrade later by purchasing an upgraded slider and/or additional image detectors. The system can automatically detect the upgrades and update the system installation information. Installation information is then used before, during, and/or after the imaging scan to position the components of the system. Such modifications can be made to other embodiments in the system, including those of FIG. 11 and FIG. 12.

Figure 11:
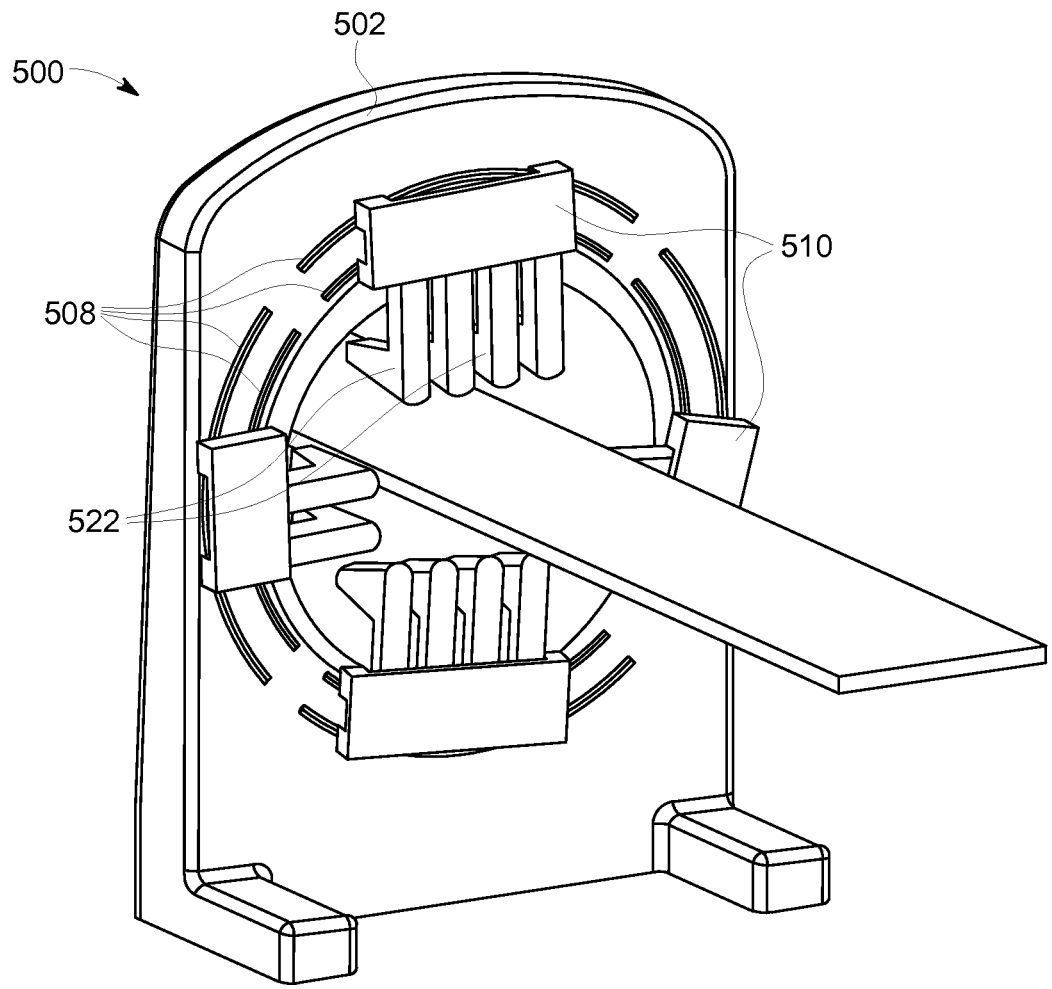
FIG. 11 is a perspective view of a gantry system with curved rails supporting linear detectors, in accordance with an embodiment.

FIG. 11 is a perspective view of a gantry system with curved rails supporting linear detectors, in accordance with an embodiment. Gantry system 500 includes stator 502, curved rails 508, curved sliders 510, and image detectors 522. Curved rails 508 attach to stator 502 and provide movement anchors for curved sliders 510. Curved rails 508 are shown in an embodiment as four separate segments around the bore of the gantry system. In alternate embodiments, curved rails 508 may be one continuous ring, two segments, three segments, or more than four. Curved sliders 510 support the attachment of one or more image detectors 522. Curved sliders 510 allow for rotational movement of image detectors 522 without a rotor and main bearing needed. Image detectors 522 include detector heads that extend into the bore of stator 502. Image detectors 522 are shown in a linear arrangement with respect to other image detectors on their respective curved slider 510.

Figure 12:
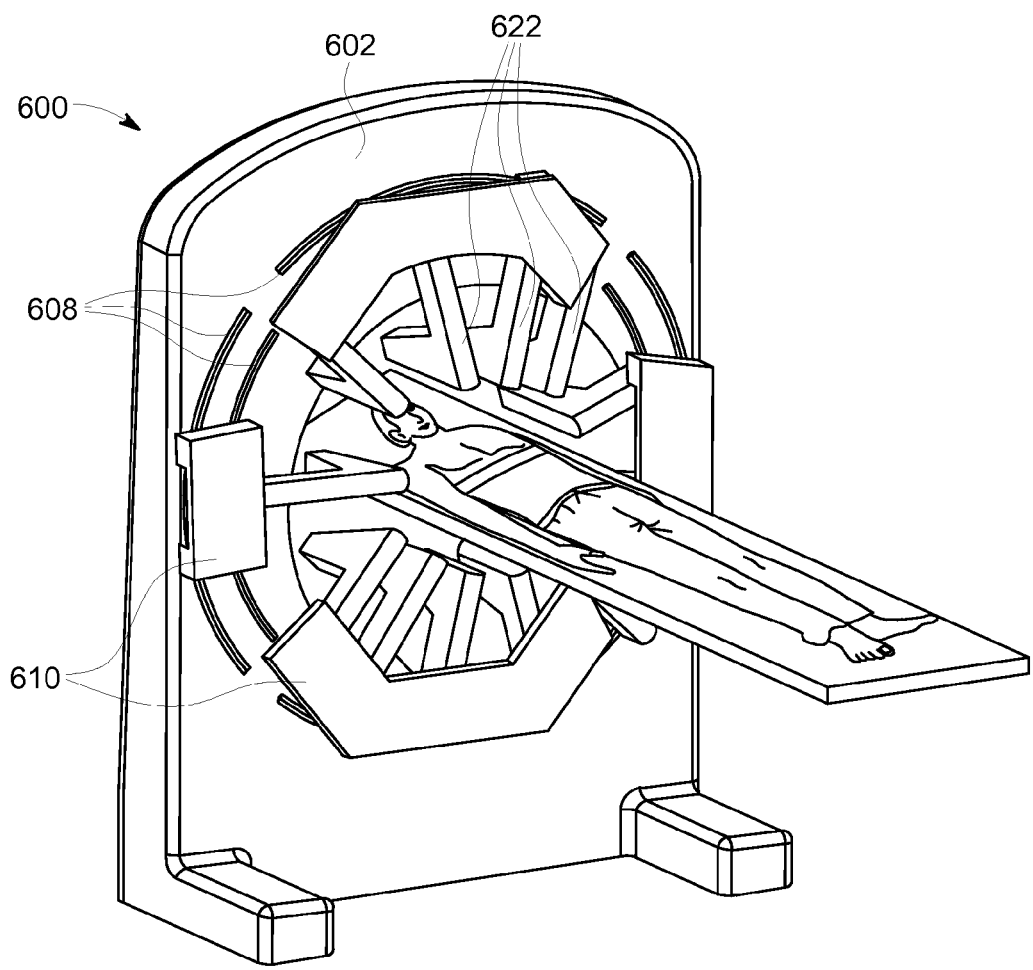
FIG. 12 is a perspective view of a gantry system with curved rails supporting radial detectors, in accordance with an embodiment.

FIG. 12 is a perspective view of a gantry system with curved rails supporting radial detectors, in accordance with an embodiment. Gantry system 600 includes stator 602, curved rails 608, sliders 610, and image detectors 622. Curved rails 608 are attached to stator 602. Sliders 610 are movably attached to curved rails 608. Image detectors 622 extend radially out from sliders 610. Image detectors 622 include detector heads that extend into the bore of stator 602. In an imaging operation, image detector heads can have their positions adjusted by detector head pivoting, detector arm extension or retraction, and/or image detector angle adjustment due to slider movement.

The term carriage refers to a movable part of the gantry system for supporting some other movable object, such as an image detector. Carriage may include the movable support members, rotors, and sliders discussed throughout.

The gantry systems of various embodiments are compact, allowing for smaller total bores which may increase patient comfort. Serviceability of components is improved as detectors can be swapped out and accessed more easily. Gantry system size may also be reduced as a result of the compact gantry system.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a flash memory disk drive, optical disk drive, and the like. The storage device may also be other similar means for loading computer programs or other instructions into the computer or processor.

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A gantry system, comprising:
a stator comprising a bore therethrough;
a carriage moveably attached to the stator;
a plurality of image detectors, each image detector having a detector arm attached to the carriage and a detector head extending from the detector arm in an L-shape configuration;
wherein the detector head, for at least one image detector, extends into the bore of the stator in the z-direction while the detector arm, for the at least one image detector, is outside of the bore of the stator in the z-direction.

2. The gantry system of claim 1, wherein the carriage comprises:
a rotor with a rotor bore therethrough, said rotor attached to said stator such that the stator bore and rotor bore create a combined bore; wherein the rotor rotates around the axis of the combined bore; and
wherein each detector arm extends into the bore of the rotor but does not extend into the bore of the stator.

3. The gantry system of claim 1, further comprising:
a rail attached to the stator;
wherein the carriage comprises a slider such that the slider is movably attached to the rail.

4. The gantry system of claim 1, wherein the carriage comprises:
a movement member that is movably attached the stator; and
wherein the movement member is straight, and a plurality of the image detectors are perpendicularly attached to the movement member.

5. The gantry system of claim 1, wherein:
the image detectors are linearly attached to the carriage.

6. The gantry system of claim 1, wherein:
the image detectors are radially attached to the carriage.

7. The gantry of claim 1, wherein:
at least some of the plurality of image detectors are configured to acquire Single Photon Emission Computed Tomography (SPECT) data.

8. The gantry system of claim 1, wherein:
at least some of the plurality of image detectors are configured to acquire Positron Emission Tomography (PET) data.

9. The gantry system of claim 1, wherein:
at least one detector head is pivotable with respect to its detector arm.

10. The gantry system of claim 1, further comprising:
a table for positioning a subject of an imaging scan;
an image reconstruction device; and
wherein the image detectors detect emission data from a subject of an imaging scan who has been placed on the table and the system reconstructs an output image from detected emission data.

11. The gantry system of claim 1, wherein:
each detector arm can extend and retract; and
each detector head can pivot its angle.

12. The gantry system of claim 11, further comprising:
a controller unit to control the movement of the carriage, extension and retraction of an image detector arm, and pivoting of an image detector head;
wherein the controller unit may control the carriage, image detector arm, and image detector head based on installation information, an imaging protocol, or user input.

13. The gantry system of claim 1, further comprising:
an image reconstruction device;
an operator console;
wherein:
- an imaging operation is initiated by the operator console;
- the gantry system performs the imaging operation by receiving emission data from the image detectors and moving at least one of the carriage, a detector arm, or a detector head during the imaging operation to detect emission data at multiple view angles;
- the gantry system sends the emission data at multiple view angles to the image reconstruction device; and
- the image reconstruction device reconstructs the emission data into an output image for display on the operator console.

14. The gantry system of claim 13, wherein:
at least one image detector is extended and activate for the imaging operation; and
at least one image detector is retracted and inactive for the imaging operation.

15. The gantry system of claim 1, wherein:
the plurality of image detectors includes at least ten image detectors.

16. The gantry system of claim 1, further comprising:
a second carriage movably attached to the stator;
a second plurality of image detectors attached to said second carriage; and
wherein the second plurality of image detectors is of a different amount than the first plurality of image detectors attached to the first carriage.

17. The gantry system of claim 1, further comprising
a second carriage movably attached to the stator with a second plurality of image detectors attached thereto;
a third carriage movably attached to the stator with a third plurality of image detectors attached thereto;
a fourth carriage movably attached to the stator with a fourth plurality of image detectors attached thereto; and
wherein each detector head of all image detectors extend into the bore of the stator in the z-direction.

18. An imaging method, comprising:
receiving an imaging operation request;
beginning an imaging operation by receiving emission data from a plurality of image detectors at a first imaging position;
instructing the movement of a carriage movably attached to a gantry stator, wherein the stator has a bore therethrough, wherein the plurality of image detectors are attached to the carriage such that the image detectors are moved to a second imaging position;
continuing the imaging operation by receiving emission data from the plurality of image detectors at the second imaging position;
wherein each image detector has a detector arm attached to the carriage and a detector head extending from the detector arm in an L-shape configuration; and
wherein the detector head, for at least one image detector, extends into the bore of the stator in the z-direction while the detector arm, for the at least one image detector, is outside of the bore of the stator in the z-direction.

19. The imaging method of claim 18, wherein:
the carriage comprises a rotor, a slider, or movement member.

* * * * *